United States Patent [19]

Lavigne

[11] 4,055,531
[45] Oct. 25, 1977

[54] PVC PLASTICIZED WITH TETRACARBOXYLATES

[75] Inventor: Joe B. Lavigne, Oakland, Calif.

[73] Assignee: Chevron Research Company, San Francisco, Calif.

[21] Appl. No.: 729,323

[22] Filed: Oct. 4, 1976

Related U.S. Application Data

[60] Division of Ser. No. 537,051, Dec. 27, 1974, Pat. No. 4,012,438, which is a continuation-in-part of Ser. No. 163,534, July 9, 1971, abandoned, which is a continuation-in-part of Ser. No. 835,735, June 23, 1969, abandoned, Ser. No. 835,736, June 23, 1969, abandoned, and Ser. No. 835,763, June 23, 1969, abandoned.

[51] Int. Cl.² .............................................. C08K 5/11

[52] U.S. Cl. ..................... 260/31.8 B; 252/56 D; 252/56 S; 260/537 N; 260/537 R; 260/346.74; 560/1; 560/190

[58] Field of Search ................................. 260/31.8 B

[56] References Cited

U.S. PATENT DOCUMENTS

| 2,561,232 | 7/1957 | Rudel et al. | 260/485 |
|---|---|---|---|
| 2,806,011 | 9/1957 | Dozzi | 260/485 R |

Primary Examiner—Stanford M. Levin
Attorney, Agent, or Firm—D. A. Newell; John Stoner, Jr.

[57] ABSTRACT

Anhydrides and esters of alkyl or cycloalkyl tetracarboxylic acids and polyvinyl chloride plastic compositions containing said esters as plasticizers.

4 Claims, No Drawings

PVC PLASTICIZED WITH TETRACARBOXYLATES

BACKGROUND OF THE INVENTION

1. Field of the Invention

This invention relates to polycarboyxlic acid compositions. More particularly, the invention is concerned with anhydrides and esters of alkyl or cycloalkyl tetracarboxylic acids which esters are useful as plasticizers in polyvinyl chloride plastic compositions.

2. Description of the Prior Art

Resins such as polyvinyl chloride and its copolymers are widely employed in the field of plastics materials. Such resins are generally hard and somewhat brittle by nature, and it is customary to add plasticizing agents to improve their workability during forming operations. Ordinarily some of the plasticizer is retained in the product formed where it characteristically provides certain desirable properties to the product. Among these characteristics is the ability of the plasticizer to impart low-temperature flexibility. Also the plasticizer must be characterized by low volatility to prevent its loss by evaporation. Furthermore, the plasticizer should be compatible with the resin and resist extraction when contacted with hydrocarbons or water. Vinyl chloride polymers in particular have been plasticized with tetra-alkyl alkenyl tetracarboxylates which are addition products of dialkyl fumarates and dialkyl alkenyl succinates. See, for instance, U.S. Pat. No. 2,806,011.

Esters of polycarboxylic acids have been suggested for use as synthetic lubricants. In general, they are characterized by higher viscosity indices, lower pour points and higher flash points and mineral oils of corresponding viscosity. Dialkyl alkenyl succinates prepared from the alkenyl succinic acid anhydride in particular have been suggested for this purpose. see, for instance, U.S. Pat. No. 2,561,232.

SUMMARY OF THE INVENTION

In accordance with the present invention, there are provided useful new alkyl or cycloalkyl tetracarboxylic acid compounds of the formula

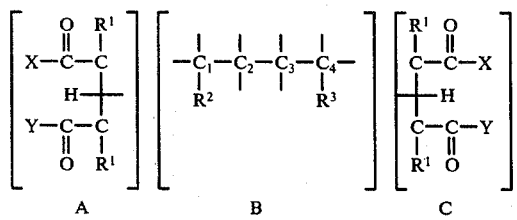

wherein A and C are monovalent succinic acid groups having attachment to B at either of the two carbon atoms of A or C having unsatisfied valences and a hydrogen atom attached to the other unsatisfied carbon atom; and wherein B is a connecting alkane or cycloalkane group of 4 to 30 carbon atoms having 2 of the above-described monovalent groups A and C, which may be the same or different, attached at carbon atoms 1 and 2 or at carbon atoms 1 and 3; and optionally having carbon atom 1 and carbon atom 4 connected by a 1–8 carbon methylene bridge; the remainder of the unsatisfied carbon valences of said bivalent hydrocarbon group being attached to hydrogen atoms; and wherein $R^1$ is H and $R^2$ and $R^3$ are H or the same or different hydrocarbyl groups; X and Y together are —O— or X and Y are the same or different groups having the structure: —OR, in which R is H or the same or different alkyl or cycloalkyl groups having from 1 to 8 carbon atoms each.

The present invention also relates to polyvinyl chloride plastic compositions containing the above-described esters in amounts sufficient to impart plasticizing properties.

DESCRIPTION OF THE PREFERRED EMBODIMENTS

The tetracarboxylic acid compounds in accordance with this invention as described above may contain from about 4 to about 30 carbon atoms in the connecting alkyl or cycloalkyl group B. For present purposes, it is preferred to react monoolefinic straight-chain aliphatic or cycloaliphatic hydrocarbons with the dicarboxylic acid compounds to give the desired alkenyl or cycloalkenyl bis(succinic anhydride), hereinafter termed "ABSA". The alkyl or cycloalkyl bis(succinic anhydride) or alkyl or cycloalkyl bis(succinic acid) which may be used to provide the tetra-alkyl or tetracycloalkyl esters of this invention is suitably obtained by the reduction of the alkenyl or cycloalkenyl groups by hydrogenation to the corresponding alkyl or cycloalkyl group. Monoolefinic aliphatic hydrocarbons of from about 4 to 20 carbon atoms are preferred for ease of purification of the tetracarboxylic acid compound product thereof.

The olefinic hydrocarbons may be linear or cyclic in nature. The unsaturation may be either terminal, as in the case of alpha-olefins, or internal, as in the case of beta, gamma and other such olefins. It is also possible for the monoolefinic hydrocarbon reactants to have various nonreactive substituents. Such substituents include the halogens, for example chlorine and bromine, nitro groups, aryl groups, alkoxy groups, carboalkoxy groups and the like.

Illustrative linear straight-chain and branched-chain olefins include: 1-butene, 2-butene, 3-hexene, 2-octene, 2,2,4-trimethylpentene-3, diisobutylene, 4-methyloctene-1, 7-dodecene, 8-eicosene, 1-triacetene, and the like. Illustrative cycloaliphatic olefinic hydrocarbons include: cyclopentene, cyclohexene, 4-methylcyclopentene, 4-ethylcyclohexene, 1-methyl-4-ethylcyclohexene and the like.

The dicarboxylic acid compounds are characterized by having the carboxyl groups or derivatives thereof in the 1,4-position and unsaturation in the 2,3-position. Such acid compounds are illustrated by maleic acid and citraconic acid as well as anhydrides thereof. Fumaric acid and mesaconic acid are also illustrative.

The unsaturated dicarboxylic acid derivatives as described, for example, dialkyl maleate such as dimethyl maleate, may be reacted as such with the olefinic hydrocarbon. However, for present purposes, it is preferred to react the unsaturated dicarboxylic acid or its anhydride with the olefinic hydrocarbon and then prepare the corresponding derivative from the tetracarboxylic acid or dianhydride, as the case may be.

The reaction of the monoolefinic hydrocarbon with unsaturated dicarboxylic acid compound is thermal and non-catalytic. The reactants are heated at a temperature of at least about 150° C. Since thermal decomposition of many alkenyl bis(succinic anhydrides) to spirodilactones occurs at about 250° C., the preferred temperature range is from about 200° to about 250° C. in the case of the acid anhydrides.

The reaction of the olefinic hydrocarbon and the unsaturated dicarboxylic acid compound occurs at various pressures. For example, atmospheric pressure is satisfactory for the higher-molecular-weight reactants which are in liquid state at reaction temperature. On the other hand, lower-molecular-weight hydrocarbons and acid compounds are reacted in closed vessels under autogenous pressures. Where desired, higher pressures may be obtained using inert gases. The process may be either batch or continuous.

The proportions of olefinic hydrocarbon and unsaturated dicarboxylic acid compound may vary from 2 mols of dicarboxylic acid to about 1 mol of olefinic hydrocarbon up to about 1 mol of dicarboxylic acid compound for each carbon in the olefinic hydrocarbon. Preferably 2 mols of unsaturated dicarboxylic acid compound are reacted with 1 mol of olefinic hydrocarbon. The reaction time varies from a few minutes to several hours. Some reaction will occur in as short a time as 10 minutes. On the other hand, reaction times of from 50 to 60 hours may be indicated. For present purposes, reaction is carried out in a period of from about 2 to about 8 hours for optimum yield and minimization of undesirable side reactions and by-products.

The reaction of monoolefinic hydrocarbon and unsaturated dicarboxylic acid compounds may be carried out by a single-step procedure where the entire amounts of reactants are heated together. However, it is advantageous to employ a multi-step procedure in which excess olefinic hydrocarbon, up to a 10:1 mol ratio of olefin to dicarboxylic acid compound, is unsaturated dicarboxylic acid compound to give the monoalkenyl dicarboxylic acid compound as the monoadduct of the first step. The excess olefin is then distilled from the monoadduct of the first step and a second mol of unsaturated dicarboxylic acid compound is adducted to give hydrocarbyl polycarboxylic acid product having an average of at least 4 carboxyl groups per molecule. In like manner, additional unsaturated dicarboxylic acid compound or corresponding 2,3-unsaturated monocarboxylic acid compound of 3 to 7 carbon atoms such as acrylic acid, methacrylic acid, methyl methacrylate, etc. may be added.

In carrying out the reaction of the olefinic hydrocarbon and unsaturated dicarboxylic compound mixing may be used to provide proper contact of the reactants. Polymerization inhibitors to prevent undesirable side reaction of the olefinic hydrocarbon and the unsaturated dicarboxylic acid compounds are also useful such as hydroquinone, orthocresol, or butylated hydroxytoluene. Also, it may be desirable to maintain low conversion rates of 50% or less and to recycle the unreacted materials in the reaction. This avoids overlong reaction periods which lead to undesirable by-products as evidenced by poor color.

The hydrocarbyl tetracarboxylic acid product of the process of this invention may be used as it comes from the reaction. However, in most instances it is desirable to remove unreacted hydrocarbon and other materials by such means as fractional distillation, solvent extraction, decantation and the like.

Certain modifications of the hydrocarbyl polycarboxylic acid product of the process of the present invention may also be contemplated. For example, the alkenyl group may be halogenated, epoxidized or hydrogenated. Also the carboxyls may be reduced to provide hydroxy analogs useful in the preparation of polysulfates and other derivatives having a variety of surface-active properties.

Hydrogenation of the double bond of the alkenyl group is readily accomplished by any of the well-known hydrogenation processes. Catalytic hydrogenation is preferred. See, for instance, the "Catalytic Hydrogenation" section et. seq. at pages 10–25, inclusive of the text entitled "Organic Preparations" by Weygand, published 1945 by Interscience Publishers, Inc., New York. Satisfactory catalysts include those containing nickel, platinum or palladium in either the free or supported state. Raney nickel is a particularly preferred unsupported catalyst. Supported catalysts include platinum on kieselguhr, palladium on carbon, etc.

The following examples illustrate the process according to the present invention and products derived therefrom. These examples are in no manner intended to limit the invention described. Unless otherwise indicated, percentages are on a weight basis.

EXAMPLE 1

Preparation of Octenyl Succinic Anhydride

A 1-gallon stirred autoclave was flushed with nitrogen and then charged with 1,800 g. (16.05 mols) of octene-1, 1,136 g. (11.6 mols) of maleic anhydride, and 20 g. of p-hydroquinone. The autoclave was closed and heated for 19 hours at 200° C. At the end of this time, the reaction mixture was charged to a Rotovac apparatus operating at 50° C. and 20 mm. of pressure, wherein 573.3 g. (5.12 mols) of octene-1 were removed. The concentrated reaction mixture was next charged to a wiped-film evaporator operating at 150° C. under 0.1 mm. of pressure. In this way there was obtained 736 g. (8.23 mols) of octenyl succinic anhydride, 23.3 g. (0.21 mol) of octene-1, and 479.6 g. of high-boiling bottoms. Based on 100% conversion of maleic anhydride, the yield of octenyl succinic anhydride was 71% (mol). The product was a pale yellow, viscous liquid.

This product had an NMR spectrum consistent with the structure of octenyl succinic anhydride. The infrared spectrum showed strong adsorption at 1,790 and 1,875 cm$^{-1}$. Analysis calculated for $C_{12}H_{18}O_3$: C, 68.54%, H, 8.62%; Found: C, 68.44%, H, 8.60%.

EXAMPLE 2

Preparation of Octenyl Bis(Succinic Anhydride)

A 1-liter, 3-necked round-bottom flask, equipped with a stirrer, a thermometer, a gas inlet tube, and a reflux condenser was flushed with nitrogen. It was then charged with 383 g. (1.82 mols) of octenyl succinic anhydride and 100 g. (1.0 mol) of maleic anhydride. The contents of the flask were heated under nitrogen with stirring for 16 hours at 200° C. At the end of this time, the resulting solution was charged to a wiped-film evaporator operating at 135°–140° C. under 0.075 mm. of pressure. In this way there was obtained 179 g. (0.85 mol) of distilled overhead, identified as octenyl succinic anhydride and 293 g. (0.95 mol) of undistilled octenyl bis(succinic anhydride). There was no recovery of unconverted maleic anhydride. Therefore, the yield of octenyl bis(succinic anhydride) based on maleic anhydride consumed was 95%.

This product was a low melting semisolid. It was purified by vacuum sublimation of 100° C. and 10$^{-5}$ mm. pressure. The NMR spectrum was consistent with octenyl bis(succinic anhydride). Infrared spectra showed strong adsorption at 1,710, 1775 and 1,865 cm$^{-1}$. The sublimed material was a tacky semisolid. Analysis calculated for $C_{16}H_{21}O_6$: C, 62.3%, H, 6.53%; Found: C, 62.1%, H, 6.46%.

Table I which follows is a compilation of other alkenyl bis(succinic anhydrides) prepared essentially as in Examples 1 and 2.

operating at 240°–250° C. and 0.1 mm. of pressure. The ester, 68 g. (0.119 mol), was taken overhead as a very pale yellow viscous oil. Analysis was consistent with the tetrabutyl structure.

The following Table II is a compilation of esters prepared from the alkenyl bis(succinic anhydrides) of this invention by procedures essentially the same as Exam-

TABLE I

ALKENYL BIS(SUCCINIC ANHYDRIDES)

| Ex. No. | Olefin Name | Grams | Maleic Anhydride Grams | Reaction Conditions T° C | Reaction Conditions Hr | Alkenyl Succinic Anhydride Recovered Grams | Alkenyl Succinic Anhydride Charged Step 2 Grams | Maleic Anhydride Grams | Reaction Conditions T° C | Reaction Conditions Hr | Alkenyl Bis-(Succinic Anhydride) Grams |
|---|---|---|---|---|---|---|---|---|---|---|---|
| 3 | Cyclohexene | 500 | 294 | 200 | 19 | 378 | 218 | 67 | 200 | 17 | 81 |
| 4 | $C_{15}$–$C_{20}$ Isomerized Olefin | Commercial Sample | | | | 450 | 66 | | 220 | 8 | 389 |
| 5 | Octene-2 | 550 | 250 | 200 | 22 | 138 | 201 | 50 | 250 | 18 | 63 |
| 6 | Penetene-1 | 256 | 179 | 200 | 19 | 112 | 111 | 32 | 200 | 4 | 59 |
| 7 | 2-Methylpentene-2 | 420 | 245 | 200 | 19 | 337 | 300 | 85 | 200 | 7 | 124 |
| 8 | Octenes[1] | 220 | 98 | 200 | 16 | 149 | 140 | 34 | 205 | 8 | 84 |
| 9 | Diisobutylene | 224 | 98 | 200 | 19 | 187 | 118 | 45 | 200 | 24 | 87 |
| 10 | Dodecene-1 | 336 | 98 | 200 | 19 | 200 | 532 | 98 | 230 | 22 | 119 |
| 11 | $C_7$–$C_9$ Alpha-Olefin | 500 | 142 | 200 | 19 | 272 | 300 | 98 | 210 | 7 | 184 |

[1]Equilibrium mixture of n-octenes ples 12 and 13.

TABLE II

ESTERS OF ALKENYL BIS(SUCCINIC ANHYDRIDES)

| Ex. No. | Alkenyl Bis-(Succinic Anhydride) Alkenyl Group | Tetraesters | | | |
|---|---|---|---|---|---|
| 14 | Pentenyl | | n-Butyl | | |
| 15 | Cyclohexenyl | | n-Butyl | | |
| 16 | Octenyl | Methyl | n-Butyl | n-Octyl | |
| 17 | $C_{15}$–$C_{20}$ Alkenyl | Methyl | | | |
| 18 | $C_7$–$C_9$ Alkenyl | Methyl | n-Butyl | n-Octyl | Isobutyl |
| 19 | Dodecenyl | | n-Butyl | | |
| 20 | Octadecenyl | | n-Butyl | | |

EXAMPLE 12

Preparation of Tetramethyl Octenyl Bis(Succinate)

Octenyl bis(succinic anhydride), 50 g. (0.163 mol), was heated at reflux in 200 ml. of methanol for 18 hours, then 2 ml. of conc. $H_2SO_4$ was added to the solution which was heated at reflux for 6 hours. The cooled mixture was poured into 1 liter of water. The organic layer was separated, dried and then distilled at 190°–210° C. at 0.6 mm. of pressure to afford 58.5 g. (0.145 mol) of product.

The tetramethyl ester was obtained as an oil. The NMR spectrum was consistent with the assigned structure. Infrared analysis showed strong adsorptions at 1,740, 1,440 and 1,165 cm$^{-1}$. Analysis calculated for $C_{20}H_{32}O_8$: C, 59.98%, H, 8.05%; Found: C, 60.04%, H, 7.89%.

EXAMPLE 13

Preparation of Tetrabutyl Octenyl Bis(Succinate)

50 g. (0.163 mol) of octenyl bis(succinic anhydride) was heated at reflux for 18 hours in a solution of 3 g. of p-toluene sulfonic acid and 150 ml. of 1-butanol in 150 ml. dry toluene. Water from the esterification reaction was collected in a Dean-Stark moisture receiver. When the theoretical amount of water was collected, heating was stopped and the solution cooled, washed with three 50 ml. portions of 10% NaOH solution, then two ml. portions of water. The organic layer was dried over $MgSO_4$, filtered, toluene and unreacted butanol were removed from the solution by means of a rotary evaporator at 70° C. and 20 mm. pressure. The residual oil was purified by passing it through a wiped-film evaporator The vinyl chloride polymer compositions of the invention contain the esters of hydrocarbyl tetracarboxylic acid in amounts sufficient to impart plasticizing properties. The quantity of plasticizer depends upon the particular polymer to be plasticized and upon its molecular weight. However, it is generally found that from about 5 to about 50 percent by weight of plasticizer based on the total polymer composition will be satisfactory from the standpoint of overall utility.

The vinyl chloride polymers of the composition are a well known class of materials. Such materials include polyvinyl chloride and the copolymers of at least 70 percent by weight of vinyl chloride with other unsaturated monomers including vinyl acetate, vinylidene chloride, etc.

In further illustration of the vinyl chloride polymer compositions according to the present invention, several compositions were prepared and subjected to typical tests for evaluation of their properties. These compositions and the test results are given in the following Table III.

In the test mixtures, 40 g. of polyvinyl chloride were combined in molten form with 20 g. of the plasticizer to be tested and 0.8 g. of a conventional barium-cadmium stabilizer (Thermolite 116).

The compositions were tested for weight loss under heat conditions by aging in an oven at 88° C. The aging process was carried out in circulating air and lasted for 64 hours. Tests were also carried out on the vinyl chloride polymer compositions to demonstrate resistance to extraction by hydrocarbons and water. In these tests, specimens of the vinyl chloride polymer compositions were placed in kerosene or in water in closed jars. The kerosene jars were maintained at 50° C. for 24 hours and the water jars were maintained at 50° to 55° C. for 24 hours. The percent weight loss of plasticizer was determined by the initial and final weights of the specimens.

The flexibility characteristics were determined by observing the lower temperature limit of usefulness in accordance with the standard method outlined in ASTM D 1043-61T. In this test, the torsional flexibility of the plastic is determined at various temperatures and the temperature at which the vinyl composition exhibits an arbitrarily established minimum flexibility is noted as the low temperature flexibility of the composition.

The Shore hardness of the vinyl chloride composition is determined in accordance with the standard method using the Shore instrument (ASTM D 676-49T). In this test, the hardness is determined in units of from 1 to 100, according to its resistance to penetration by a standard needle which is applied to the composition under a stadard load for a standard length of time. The lower numbers indicate the harder compositions having greater resistance to penetration.

pressure of 50 psi. At the end of 42 hours, 80% of the theoretical pressure drop was realized, and no more hydrogen was taken up even after the addition of fresh catalyst. The catalyst was then removed by filtration and dioxane removed under reduced pressure by means of a rotary evaporator to leave 31.6 g of brown, tacky residue. A small portion of this material was purified by high vacuum sublimation (130° C at $5 \times 10^{-3}$ mm Hg) and obtained as a colorless semisolid. Analysis calculated for $C_{16}H_{22}O_6$: C, 62.32%; H, 6.53%. Found: C, 66.46%, H, 7.79%.

In addition to providing flexibility to the final plastic object, a satisfactory plasticizer must not change the color of the plastic; and it must not be easily removed by either volatilization or extraction. Tests have been devised to measure all of the above properties. Surprisingly, extractability by soapy water or kerosene is less for the hydrogenated ABSA as compared to ABSA. The following runs illustrate this effect.

PVC test blanks were prepared by mixing 40 parts of PVC, 20 parts of the test plasticizer, and 0.8 part of a stabilizer (tin stearate) in a Brabender mixer until homo-

TABLE III

TETRAESTERS OF ALKENYL BIS(SUCCINIC ANHYDRIDE) AS PLASTICIZERS

| Ex. No. | Alkenyl Group | Tetra-ester | Oven Aging Wt. Loss % | Extraction By Kerosene % | Extraction By H$_2$O % | Flexibility Temperature ° C. | Shore Hardness |
|---|---|---|---|---|---|---|---|
| 21 | Dioctyl phthalate | — | 1.0 | 8.0 | 0.2 | −27 | 83 |
| 22 | Tri(octyl/decyl) mellitate[1] | — | 0.8 | 13.1 | 0.2 | −26 | 91 |
| 23 | Pentenyl | n-butyl | 1.6 | 3.1 | 0.3 | −19 | 82 |
| 24 | Octenyl | n-butyl | 0.7 | 4.8 | 0.3 | −22 | 85 |
| 25 | Octenyl | methyl | 1.4 | 2.3 | 1.4 | −12 | 86 |
| 26 | C$_7$–C$_9$ alkenyl | i-butyl | 7.5 | 9.0 | 0.3 | −28 | 82 |
| 27 | C$_7$–C$_9$ alkenyl | n-butyl | 0.9 | 6.5 | 0.3 | −24 | 84 |
| 28 | C$_7$–C$_9$ alkenyl | methyl | 4.1 | 5.5 | 5.9 | −15 | 87 |
| 29 | Hydrogenated octenyl | n-butyl | 3.0 | 5.4 | 0.3 | −25 | 83 |
| 30 | Dodecyl | methyl | 1.6 | 4.3 | 0.7 | −17 | 87 |
| 31 | C$_{15}$–C$_{20}$ alkenyl | methyl | 0.8 | 1.9 | 0.3 | −13 | 89 |

[1]Prepared from a commercial mixture of octanol and decanol

In the above table, Examples 1 and 2 were dioctyl phthalate and octyl/decyl trimellitate, respectively. These are widely accepted commercial plasticizers and were included in the evaluations for the purpose of comparison.

Hydrogenation of alkenyl or cycloalkenyl bis anhydride, acid or ester to the corresponding alkyl or cycloalkyl connecting group is illustrated by the following examples.

EXAMPLE 32

Hydrogenation of Octenyl bis-(Succinic Acid)

A 10-g sample of octenyl bis(succinic acid) was hydrogenated in 120 ml of water over approximately 4 g of W-2 Raney nickel catalyst at an initial H$_2$ pressure of 50 psi for 14 hours. Slightly more (110%) of the theoretical pressure drop was realized at the end of this time. The catalyst was removed by filtration and water under reduced pressure by means of a rotary evaporator. The residue was dried in a vacuum desiccator over P$_2$O$_5$ for several days to afford a white deliquescent powder which was not further characterized.

EXAMPLE 33

Hydrogenation of Octenyl bis(Succinic Anhydride)

Octenyl bis(succinic anhydride) (31 g [1 mol]) in 150 ml anhydrous dioxane was hydrogenated over 3 g of 5% palladium-on-carbon catalyst at an initial hydrogen geneity was obtained. The resulting mixture was extruded into sheets, which were cut into appropriate-size test swatches. Different swatches, from the same blended mixture, were tested for: (1) color, (2) flex temperature, (3) tensile properties, (4) hardness, (5) volatility, and (6) extractability. The results are shown in Table V Long-term soapy water extraction tests were carried out at 70° C. on swatches of PVC containing the tetra-n-butyl ester of octenyl-bis(succinic acid) and the corresponding hydrogenated compound. The results were as follows in Table IV:

TABLE IV

| | Weight Loss, % | | |
|---|---|---|---|
| Time, hrs | Unsaturated Compound | Saturated Compound | Commercial Dioctyl Phthalate |
| 50 | 6 | 3 | 8 |
| 120 | 12 | 6 | 17 |
| 190 | 16 | 10 | 20 |

The above results, and particularly those of the long-term soapy water extraction tests, show that the hydrogenated ABSA compounds have a surprisingly low solubility as compared to the unsaturated ABSA compounds. This improvement in resistance to extraction by soapy water due to two additional hydrogens in the molecule is wholly unpredictable and, therefore, unexpected.

TABLE V

| | | | | Plasticized PVC Sheet | | | | | | |
|---|---|---|---|---|---|---|---|---|---|---|
| | | | | Tensile Properties[3] | | | | Vola- | Extraction Loss | | |
| | Identity | | Flex | 100% Modu- | Break | Break Elon- | Hardness | tility | Kero- | Water | |
| Run No. | Tetra-n-butyl Ester of | Color[1] | Temp.,[2] °C | lus, psi | Strength, psi | gation, % | Shore A,[4] 10 Sec. | Loss,[5] % | sene,[6] % | Distilled,[7] % | Soapy,[8] % |
| 1 | Octene-1 ABSA[9] | <1 | −22 | 1940 | 2880 | 240 | 85 | 1.7 | 4.8 | 0.3 | 6.1 |
| 2 | Hydrogenated 1[10] | 2 | −25 | 1810 | 2990 | 260 | 83 | 3.0 | 5.4 | 0.3 | —[14] |
| 3 | C$_7$-C$_9$ Alkenyl ABSA[11] | 3 | −24 | 1900 | 2920 | 240 | 84 | 0.9 | 6.5 | 0.3 | — |
| 4 | Hydrogenated 3 | <1 | −24 | 1890 | 2750 | 220 | 85 | 1.7 | 7.6 | 0.3 | 7.5 |
| 5 | Pentene-1 ABSA[12] | 3 | −19 | 1990 | 2840 | 220 | 82 | 1.6 | 3.1 | 0.3 | — |
| 6 | Hydrogenated 5 | <1 | −19 | 2110 | 3000 | 220 | 85 | 1.3 | 2.5 | 0.4 | 12.6 |
| 7 | Dodecene-1 ABSA[13] | 9 | −20 | 2000 | 2660 | 210 | 89 | 1.3 | 5.0 | 0.3 | 3.1 |
| 8 | Hydrogenated 7 | 3 | −20 | 1920 | 2510 | 200 | 89 | 1.2 | 4.5 | 0.2 | 2.4 |
| 9 | Isobutylene ABSA[13] | 7 | −24 | 1850 | 3010 | 235 | 80 | 6.8 | 8.6 | 1.6 | — |
| 10 | Hydrogenated 9 | 4 | −20 | 1800 | 2920 | 240 | 83 | 3.3 | 4.2 | 1.5 | 13.7 |
| 11 | Propylene ABSA | 4 | −26 | 2000 | 3170 | 250 | 80 | 2.2 | 10.2 | 0.5 | — |
| 12 | Hydrogenated 11 | 4 | −24 | 1710 | 2820 | 240 | 82 | 1.2 | 4.7 | 0.6 | 15.1 |
| 13 | Cyclohexene ABSA | 3 | −12 | 2010 | 2630 | 200 | 87 | 1.8 | 1.4 | 0.7 | 9.8 |
| 14 | Hydrogenated 13 | 4 | − 3 | 2370 | 2770 | 180 | 89 | 1.1 | 0.2 | 0.5 | 8.4 |

[1]Color by Gardner scale
[2]ASTM D 1043–61T
[3]ASTM D 412–64T
[4]ASTM D 1706–61
[5]After 64 hours in 83° C circulating air
[6]After 24 hours at 50° C
[7]After 24 hours at 58° C
[8]After 48 hours at 80° C
[9]Example 24
[10]Example 29
[11]Example 27
[12]Example 23
[13]Average of two runs
[14]See long-term soapy water extraction results of Table IV It will be seen from the evaluation that the vinyl chloride polymer compositions of the invention containing esters of alkyl or cycloalkyl tetracarboxylic acid have desirable chemical and physical properties when compared to the presently accepted plastics compositions of the art.

The vinyl chloride compositions of the invention, as illustrated by the above examples, may also contain other materials commonly used with such compositions along with the plasticizer. For example, stabilizer such as the salts and soaps of lead, tin, calcium, barium, zinc, lithium, as well as organo phosphites and epoxidized oils and esters and the like may be used. Also dyes, pigments, opacifiers, fillers and the like may be used.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:

1. Polyvinyl chloride plastic compositions containing in amounts sufficient to impart plasticizing properties esters of the formula

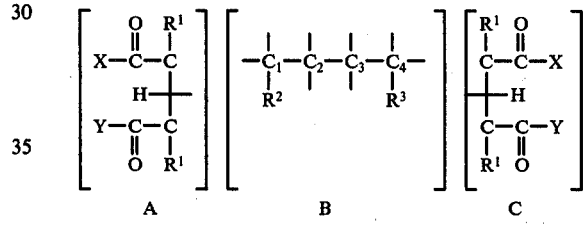

wherein A and C are monovalent succinic acid groups having attachment to B at either of the two carbon atoms of A or C having unsatisfied valences and a hydrogen atom attached to the other unsatisfied carbon atom; and wherein B is a connecting alkane or cycloalkane group of 8 to 30 carbon atoms having 2 of the above-described monovalent groups A and C, which may be the same or different, attached at carbon atoms 1 and 2 or at carbon atoms 1 and 3; and optionally having carbon atom 1 and carbon atom 4 connected by a 1–8 carbon methylene bridge; the remainder of the unsatisfied carbon valences of said bivalent hydrocarbon group being attached to hydrogen atoms; and wherein $R^1$ is H and $R^2$ and $R^3$ are H or the same or different alkyl groups; X and Y are the same or different groups having the structure: —OR, in which R is an alkyl group having from 1 to 8 carbon atoms.

2. Compositions of claim 1 in which B has 8 carbon atoms.

3. Compositions of claim 1 in which X and Y are each —OCH$_3$.

4. Compositions of claim 1 in which X and Y are each —O(CH$_2$)$_3$CH$_3$.

* * * * *